US010450240B2

(12) United States Patent
Montalbano et al.

(10) Patent No.: US 10,450,240 B2
(45) Date of Patent: *Oct. 22, 2019

(54) PROCESSES AND APPARATUSES FOR METHYLATION OF AROMATICS IN AN AROMATICS COMPLEX

(71) Applicant: UOP LLC, Des Plaines, IL (US)

(72) Inventors: Joseph A. Montalbano, Elmhurst, IL (US); R. Jason L. Noe, Mount Prospect, IL (US); Veronica G. Deak, Chicago, IL (US); Anton N. Mlinar, Vernon Hills, IL (US); Robert E. Tsai, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/809,781

(22) Filed: Nov. 10, 2017

(65) Prior Publication Data

US 2019/0144358 A1  May 16, 2019

(51) Int. Cl.
| | |
|---|---|
| *C07C 2/64* | (2006.01) |
| *B01J 19/24* | (2006.01) |
| *C07C 6/06* | (2006.01) |
| *C07C 2/86* | (2006.01) |
| *C07C 6/12* | (2006.01) |

(52) U.S. Cl.
CPC ............ *C07C 2/64* (2013.01); *B01J 19/24* (2013.01); *C07C 2/864* (2013.01); *C07C 6/06* (2013.01); *C07C 6/126* (2013.01); *B01J 2219/24* (2013.01)

(58) Field of Classification Search
CPC .......... C07C 2/64; C07C 2/864; C07C 15/08; C07C 15/00; C07C 15/16; C07C 2/00; C07C 2/868; C07C 41/05; C07C 2/66; C07C 5/321; C07C 5/41; C07C 6/126; B01J 20/18; B01J 20/28004; B01J 21/04; B01J 23/28; B01J 23/755; B01J 23/883; B01J 23/888; B01J 29/005; B01J 29/084; B01J 29/18; B01J 29/40; B01J 29/44; B01J 35/1019; B01J 35/1042; B01J 35/108
USPC ........................................ 585/321, 446, 454
See application file for complete search history.

(56) References Cited

U.S. PATENT DOCUMENTS

| | | |
|---|---|---|
| 5,601,755 A | 2/1997 | Commandeur et al. |
| 5,866,740 A | 2/1999 | Mikitenko et al. |
| 5,986,148 A * | 11/1999 | Beech, Jr. ............... C07C 41/05 568/694 |
| 5,994,603 A | 11/1999 | Mohr et al. |
| 6,111,161 A | 8/2000 | MacPherson et al. |
| 7,812,208 B2 | 10/2010 | Cheng et al. |
| 2011/0092756 A1* | 4/2011 | Lattner .................... C07C 2/864 585/446 |
| 2013/0165724 A1* | 6/2013 | Han ....................... B01J 8/1818 585/447 |
| 2013/0253245 A1* | 9/2013 | Zheng ..................... C07C 2/865 585/467 |
| 2015/0094512 A1* | 4/2015 | Gattupalli ............... C07C 7/005 585/805 |

FOREIGN PATENT DOCUMENTS

| | | |
|---|---|---|
| CN | 101410173 B | 3/2013 |
| CN | 104936931 A | 9/2015 |
| IN | 194648 B | 11/2004 |
| IN | 200701015 P1 | 4/2007 |
| WO | 1995/13998 A1 | 5/1995 |

OTHER PUBLICATIONS

Ghoreishi et. al, Modeling of para-Xylene Synthesis via Nonselective Toluene Disproportionation, International Journal of Chemical Reactor Engineering, v 7, p. 22 pp., Jan. 2009.
Wu et.al., Selective formation of p-xylene with disproportionation of toluene over MCM-22 catalysts, Microporous and Mesoporous Materials (ISSN 1387-1811) V22 N.1-3 343-56 (Jun. 17, 1998), v 22, n 1-3, p. 343-56, Jun. 17, 1998.
Gu et. al., Separation of p-xylene from multicomponent vapor mixtures using tubular MFI zeolite mmbranes, Journal of Membrane Science, v 280, n 1/2, p. 624-633, Sep. 1, 2006.
Masuda et. al., Influence of acid sites on intracrystalline diffusivities within MFI-type zeolites, Microporous and Mesoporous Materials, v 23, n 3-4, p. 157-167, Aug. 1998.
International Search Report and Written Opinion from corresponding PCT application No. PCT/US2018/059721, dated Feb. 21, 2019.

* cited by examiner

*Primary Examiner* — Sharon Pregler

(57) ABSTRACT

It is desirable to provide improved processes and apparatuses for methylation of aromatic compounds such as toluene and benzene in an aromatics complex. Described herein are processes and apparatuses for methylation of aromatics in an aromatics complex for producing a xylene isomer product. More specifically, processes and apparatuses for producing para-xylene by the selective methylation of toluene and/or benzene in an aromatics complex.

15 Claims, 1 Drawing Sheet

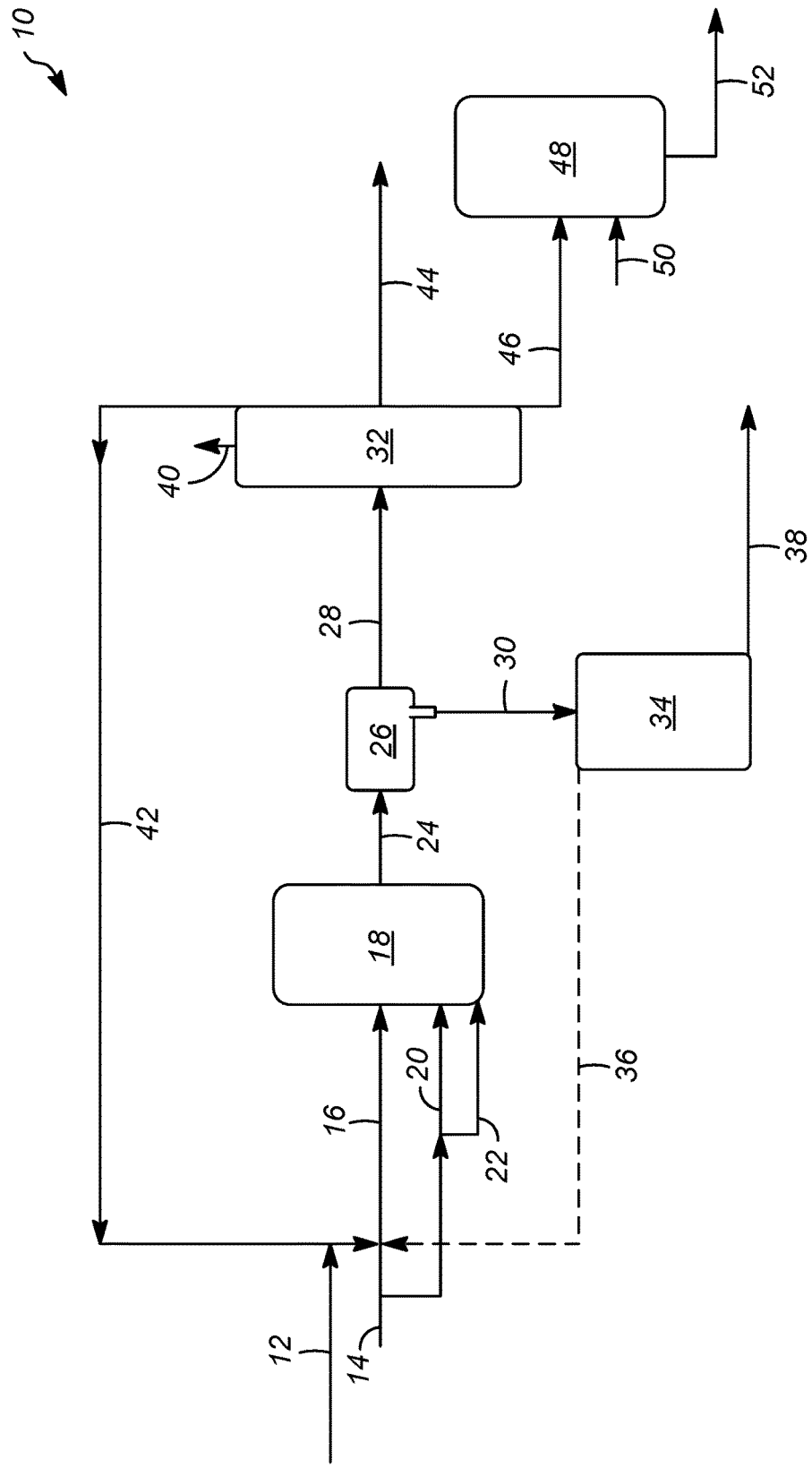

PROCESSES AND APPARATUSES FOR METHYLATION OF AROMATICS IN AN AROMATICS COMPLEX

FIELD

This present disclosure relates to processes and apparatuses for methylation of aromatics in an aromatics complex for producing a xylene isomer product. More specifically, the present disclosure relates to a process for producing para-xylene by the selective methylation of toluene and/or benzene in an aromatics complex.

BACKGROUND

Xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of C8 aromatics.

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene is de-alkylated to produce benzene or selectively disproportionated to yield benzene and C8 aromatics from which the individual xylene isomers are recovered.

An aromatics complex flow scheme has been disclosed by Meyers in the HANDBOOK OF PETROLEUM REFINING PROCESSES, 2d. Edition in 1997 by McGraw-Hill, and is incorporated herein by reference.

Traditional aromatics complexes send toluene to a transalkylation zone to generate desirable xylene isomers via transalkylation of the toluene with A9+ components. A9+ components are present in both the reformate bottoms and the transalkylation effluent.

Methylation of toluene or benzene with oxygenates such as methanol has been proposed as a pathway to make xylene and to increase the methyl to phenyl ratio in the aromatic complex to maximize xylene production. Toluene methylation operating in vapor phase has a poor feed, especially oxygenate, utilization, low aromatics conversion per pass and poor catalyst stability in a time span of hours, days and weeks, thus requiring frequent regeneration. Typically, toluene methylation is operating with selective para-xylene production objective, which requires operating under severe process conditions, namely high temperature where methanol decomposition to COx and H2 is significant, with a significant amount of diluents such as H2O and H2 and thus requires recycling a catalyst which is relatively difficult to prepare reproducibly. MFI zeolite has been the catalyst being used predominantly in this process.

Accordingly, it is desirable to provide improved methods and apparatuses for methylation of aromatic compounds such as toluene and benzene in an aromatics complex. Further, it is desirable to provide a cost-effective method and apparatus for toluene and/or benzene methylation which operates under mild conditions, promotes high utilization of the feedstock and where higher than equilibrium para-xylene to xylene can be achieved without using dilution. Also, it is desirable to reduce the overall costs of operating and/or incorporating such a methylation unit in an aromatics complex. Furthermore, other desirable features and characteristics of the present subject matter will become apparent from the subsequent detailed description of the subject matter and the appended claims, taken in conjunction with the accompanying drawings and this background of the subject matter.

SUMMARY

The present subject matter relates to processes and apparatuses for toluene and/or benzene methylation in an aromatics complex for producing xylene isomer. More specifically, the present disclosure relates to processes and apparatuses for toluene methylation under mild reaction conditions, namely a combination of low temperatures and elevated pressures.

In the foregoing, all temperatures are set forth in degrees Celsius and all parts and percentages are by weight, unless otherwise indicated. Other objects, advantages and applications of the present invention will become apparent to those skilled in the art from the following detailed description and drawing. Additional objects, advantages and novel features of the examples will be set forth in part in the description which follows, and in part will become apparent to those skilled in the art upon examination of the following description and the accompanying drawing or may be learned by production or operation of the examples. The objects and advantages of the concepts may be realized and attained by means of the methodologies, instrumentalities and combinations particularly pointed out in the appended claims.

BRIEF DESCRIPTION OF THE DRAWING

The FIGURE illustrates a process and apparatus for toluene methylation under mild reaction conditions, namely a combination of low temperatures and elevated pressures.

DEFINITIONS

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated C1, C2, C3, Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8, An where "n" represents the number of carbon atoms in the one or more aromatic molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three or more carbon atoms.

As used herein, the term "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Net overhead lines and net bottoms lines refer to the net lines from the column downstream of any reflux or reboil to the column unless otherwise shown. Stripping columns may omit a reboiler at a bottom of the column and instead provide heating requirements and separation impetus from a fluidized inert media such as steam.

As depicted, process flow lines in the drawings can be referred to interchangeably as, e.g., lines, pipes, feeds, gases, products, discharges, parts, portions, or streams.

The term "passing" means that the material passes from a conduit or vessel to an object.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The description of the apparatus of this invention is presented with reference to the attached FIGURE. The FIGURE is a simplified diagram of the preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

The various embodiments described herein relate to processes and apparatuses for toluene and/or benzene methylation in an aromatics complex for producing xylene isomer. As shown in the FIGURE, a process and apparatus 10 comprises of a first feed stream 12 comprising toluene and a second feed stream 14 comprising methanol. The first feed stream 12 and the second feed stream 14 are combined and pass to a reaction zone 18 via line 16. Additional methanol streams may be fed to the reaction zone 18 via lines 20 and 22. It is also contemplated that additional methanol streams may also be added to the reaction zone 18. Passing multiple methanol streams to the reaction zone 18 maximizes the toluene to methanol ratio and minimizes temperature rise due to reaction exotherm. The reaction zone 18 may comprise multiple reactors. The reaction zone 18 may comprise only one reactor or one reactor with interstage injection points to control the reactor exotherm, or the reaction zone 18 may comprise up to four reactors. The reaction zone 18 operates at a temperature of about 200° C. to about 400° C. The reaction zone 18 operates at a pressure of about 15 to about 400 psig.

The reaction zone product stream 24 exits the reaction zone 18 and passes to the separator 26. The reaction zone product stream 24 comprises toluene, para-xylene, and water. The separator 26 separates stream 24 into stream 28 and stream 30. Stream 28 passes to a stripper 32. Stream 30 passes to a methanol stripper 34 which provides a methanol recycle stream 36 to the reaction zone 18. The methanol stripper product stream 38 exits the methanol stripper 34 and goes to waste water treating. Sending the methanol to the methanol stripper 34 purifies the product methanol that is recycled, which is favorable for lower methanol conversions.

The stripper 32 produces an overhead stream 40 comprising vent to fuel gas, an overhead stream 42 comprising toluene and benzene that is recycled back to the first feed stream 12, a side cut 44 comprising para-xylene, toluene, ortho-xylene, meta-xylene, and some C9-C10, and a bottom stream 46 comprising C9+, which includes Diphenylmethanes. The bottoms stream 46 is passed to a transalkylation unit 48 which also receives a stream 50 comprising benzene and C9+ as well as potentially toluene. The transalkylation unit product stream 52, now containing para-xylene, exits the bottom of the transalkylation unit 48 and may be passed to a benzene column, toluene column, xylene column, para-xylene separation zone, or an isomerization zone.

TABLE 1

| | | |
|---|---|---|
| Days on stream | 3.5 | 19 |
| WHSV, hr-1 | 3.5 | 3.5 |
| H2/HC | 3.0 | 3.0 |
| WABT, ° C. | 412 | 410 |
| Pressure, psig | 400 | 400 |
| Conversion, wt % | | |
| Methyl Diphenylmethanes (with 14 carbons) | 15 | 14 |
| Methyl Diphenylmethanes (with 15 carbons) | 90 | 90 |
| Methyl Diphenylmethanes (with 16 carbons) | 78 | 80 |
| Methyl Diphenylmethanes (with 17 carbons) | 50 | 54 |

The results in Table 1 illustrate the steady conversion of diphenylmethanes from the toluene disproportionation and transalkylation unit. Because the diphenylmethanes are found to largely convert to xylenes, the stripper 32 was designed to separate these components for conversion in the transalkylation unit. Had the diphenylmethanes not been separated from the paraxylene product in the stripper 32, they would have been routed to less valuable heavy waste product.

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for the methylation of toluene, comprising passing a toluene feed stream and a plurality of methanol feed streams to a reaction zone to produce a reaction zone product stream; and separating the reaction zone product stream and passing the reaction zone product stream to a stripper to produce a vent gas stream, an overhead stream comprising toluene and xylenes, a side cut comprising xylenes and a bottoms stream comprising C9+, specifically containing diphenylmethane components. An embodiment of the invention is one, any or all of prior embodiments in this paragraph up through the first embodiment in this paragraph, wherein the toluene stream and at least one methanol stream are admixed before entering the reaction zone. An embodiment of the invention is one, any or all of prior embodiments in this paragraph up through the first embodiment in this paragraph, wherein one additional methanol stream is passed to the reaction zone. An embodiment of the invention is one, any or all of prior embodiments in this paragraph up through the first embodiment in this paragraph, wherein two additional methanol streams are passed to the reaction zone. An embodiment of the invention is one, any or all of prior embodiments in this paragraph up through the first embodiment in this paragraph, wherein three additional methanol streams are passed to the reaction zone. An embodiment of the invention is one, any or all of prior embodiments in this paragraph up through the first embodiment in this paragraph, wherein the reaction zone comprises at least one reactor. An embodiment of the invention is one, any or all of prior embodiments in this paragraph up through the first embodiment in this paragraph, wherein the reaction zone comprises no more than four reactors. An embodiment of the invention is one, any or all of prior embodiments in this paragraph up through the first embodiment in this paragraph, further comprising passing the C9+ stream to a transalkylation zone. An embodiment of the invention is one, any or all of prior embodiments in this paragraph up through the first embodiment in this paragraph, wherein the transalkyation zone operates at a temperature of about 300° C. to about 500° C. and a pressure of about 1379 kPa (about 200 psig) to about 4137 kPa (about 600 psig). An embodiment of the invention is one, any or all of prior embodiments in this paragraph up through the first embodiment in this paragraph, wherein the reaction zone operates at a temperature of at about 200° C. to about 400° C. An embodiment of the invention is one, any or all of prior embodiments in this paragraph up through the first embodiment in this paragraph, wherein the reaction zone operates at a temperature of at about 250° C. to about 350° C. An embodiment of the invention is one, any or all of prior embodiments in this paragraph up through the first embodiment in this paragraph, wherein the reaction zone operates at a pressure of about 103 kPa (about 15 psig) to about 2758 kPa (about 400 psig). An embodiment of the invention is one, any or all of prior embodiments in this paragraph up through the first embodiment in this paragraph, wherein the reaction zone operates at a pressure of about 345 kPa (about 50 psig) to about 1379 kPa (about 200 psig). An embodiment of the invention is one, any or all of prior embodiments in this paragraph up through the first embodiment in this paragraph, wherein the overhead stream comprising toluene is recycled back to the toluene feed stream. An embodiment of the invention is one, any or all of prior embodiments in this paragraph up through the first embodiment in this paragraph, further comprising separating a methanol stream from the reaction zone product stream and recycling the methanol stream back to the methanol feed stream.

A second embodiment of the invention is an apparatus for the methylation of toluene, comprising a plurality of lines comprising toluene in direct communication with a reaction zone wherein the reaction zone is also coupled to a line comprising the reaction zone product stream; the reaction zone product stream is in direct communication with a stripper to produce a line comprising a vent gas stream, an overhead line comprising toluene and xylenes, a side cut line comprising xylenes and a bottoms line comprising C9+, specifically containing diphenylmethane components. An embodiment of the invention is one, any or all of prior embodiments in this paragraph up through the second embodiment in this paragraph, wherein the reaction zone comprises at least one reactor. An embodiment of the invention is one, any or all of prior embodiments in this paragraph up through the second embodiment in this paragraph, wherein the reaction zone comprises no more than four reactors. An embodiment of the invention is one, any or all of prior embodiments in this paragraph up through the second embodiment in this paragraph, wherein the reaction zone operates at a temperature of at about 200° C. to about 400° C. An embodiment of the invention is one, any or all of prior embodiments in this paragraph up through the second embodiment in this paragraph, wherein the reaction zone operates at a pressure of about 103 kPa (about 15 psig) to about 2758 kPa (about 400 psig).

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for the methylation of toluene, comprising:
   passing a toluene feed stream and a plurality of methanol feed streams to a reaction zone to produce a reaction zone product stream; and
   separating a portion of the reaction zone product stream and passing the separated portion of the reaction zone product stream to a stripper to produce a vent gas stream, an overhead stream comprising toluene and xylenes, a side cut comprising xylenes and a bottoms stream comprising C9+, wherein the bottoms stream comprising C9+ comprises diphenylmethane.

2. The process of claim 1, wherein the toluene feed stream and at least one of the plurality of methanol feed streams are admixed before entering the reaction zone.

3. The process of claim 1, wherein one additional methanol stream in addition to the plurality of methanol streams recited in claim 1 is passed to the reaction zone.

4. The process of claim 1, wherein two additional methanol streams in addition to the plurality of methanol streams recited in claim 1 are passed to the reaction zone.

5. The process of claim 1, wherein three additional methanol streams in addition to the plurality of methanol streams recited in claim 1 are passed to the reaction zone.

6. The process of claim 1, wherein the reaction zone comprises at least one reactor.

7. The process of claim 1, wherein the reaction zone comprises no more than four reactors.

8. The process of claim 1, further comprising passing the bottoms stream comprising C9+ to a transalkylation zone.

9. The process of claim 8, wherein the transalkyation zone operates at a temperature of about 300° C. to about 500° C. and a pressure of about 1379 kPa (about 200 psig) to about 4137 kPa (about 600 psig).

10. The process of claim 1, wherein the reaction zone operates at a temperature of about 200° C. to about 400° C.

11. The process of claim 1, wherein the reaction zone operates at a temperature of about 250° C. to about 350° C.

12. The process of claim 1, wherein the reaction zone operates at a pressure of about 103 kPa (about 15 psig) to about 2758 kPa (about 400 psig).

13. The process of claim 1, wherein the reaction zone operates at a pressure of about 345 kPa (about 50 psig) to about 1379 kPa (about 200 psig).

14. The process of claim 1, wherein the overhead stream comprising toluene and xylenes is recycled back to the toluene feed stream.

15. The process of claim 1, further comprising separating a methanol stream from the reaction zone product stream and recycling the methanol stream back to one of the plurality of methanol feed streams.

* * * * *